United States Patent [19]
Ward et al.

[11] Patent Number: 5,626,618
[45] Date of Patent: May 6, 1997

[54] MECHANICAL ADJUNCT TO CARDIOPULMONARY RESUSCITATION (CPR), AND AN ELECTRICAL ADJUNCT TO DEFIBRILLATION COUNTERSHOCK, CARDIAC PACING, AND CARDIAC MONITORING

[75] Inventors: Kevin R. Ward; Charles G. Brown; Roger R. Dzwonczyk, all of Columbus, Ohio

[73] Assignee: The Ohio State University, Columbus, Ohio

[21] Appl. No.: 126,542

[22] Filed: Sep. 24, 1993

[51] Int. Cl.$^6$ .................................................. A61N 1/39
[52] U.S. Cl. .......................... 607/5; 607/124; 607/133; 128/642
[58] Field of Search ................... 637/2, 4, 5, 116, 637/119, 124, 133; 128/642

[56] References Cited

U.S. PATENT DOCUMENTS

| | | |
|---|---|---|
| 4,090,518 | 5/1978 | Elam . |
| 4,198,963 | 4/1980 | Barkalow et al. . |
| 4,640,298 | 2/1987 | Pless et al. ............... 607/124 |
| 4,706,688 | 11/1987 | Michael et al. . |
| 4,960,133 | 10/1990 | Hewson . |
| 5,056,532 | 10/1991 | Hull et al. . |
| 5,170,803 | 12/1992 | Hewson et al. . |
| 5,179,952 | 1/1993 | Buinevicius et al. . |
| 5,191,885 | 3/1993 | Bilof et al. ............... 607/124 |
| 5,197,491 | 3/1993 | Anderson et al. . |

OTHER PUBLICATIONS

McKeown et al., "Transesophageal cardioversion", *American Heart Journal*, vol. 125, No. 2, Part 1, Feb. 1993, pp. 396–404.

Primary Examiner—William E. Kamm
Assistant Examiner—Kennedy J. Schaetzle
Attorney, Agent, or Firm—Frank H. Foster; Kremblas, Foster, Millard & Pollick

[57] ABSTRACT

An apparatus for aiding in the treatment of cardiac arrest patients which includes a flexible tube having an elongated bladder attached between its opposite ends and a stomach bladder attached to its distal end. Each bladder has a conductive portion which serves as an electrode. Wires are embedded in the sidewall of the tube and connected to each electrode. Passageways formed in the sidewall of the tube and fluid-conveying tubes connected thereto form a fluid path through which a saline solution or a gas passes to fill the bladders. The tube is positioned so that the stomach bladder lies in the fundus of the stomach and the esophageal bladder lies in the posterior to the heart. The stomach bladder is filled and moderate countertraction is applied. Then the esophageal bladder is filled. The esophageal bladder serves as a platform by expanding and hardening the esophagus behind the heart. The heart is then compressed between the sternum and the hardened esophageal bladder, thus enhancing artificial circulation. A defibrillation countershock is administered through the low impedance pathway between the stomach and esophageal electrodes, which are in close proximity to the left ventricle, in order to defibrillate the heart.

22 Claims, 4 Drawing Sheets

MECHANICAL ADJUNCT TO CARDIOPULMONARY RESUSCITATION (CPR), AND AN ELECTRICAL ADJUNCT TO DEFIBRILLATION COUNTERSHOCK, CARDIAC PACING, AND CARDIAC MONITORING

TECHNICAL FIELD

This invention relates generally to methods and apparatus for treating cardiac arrest patients, patients with arrhythmias, patients undergoing cardioversion, patients in shock, patients with a need for monitoring and patients in need of cardiac pacing. More specifically, this invention relates to devices for inserting into the patient's body and methods of inserting and positioning the devices for treating these patients.

BACKGROUND ART

Approximately one million people per year have cardiac arrests in the United States. Less than 10 percent of these people are discharged from the hospital live. This percentage of people discharged would increase if the treatment available after the onset of cardiac arrest was improved. Four areas in which the treatment could be improved include artificial circulation during cardiopulmonary resuscitation (CPR), defibrillation countershock techniques, cardiac pacing and cardiac monitoring.

The heart of a human being lies between the sternum and the spinal column. The esophagus is normally a flaccid collapsed tube that lies in the midline of the body between the heart and the spinal column. The anterior surface of the esophagus contacts the posterior surface of the heart and particularly the left ventricle of the heart. The descending aorta is adjacent to the esophagus and the heart and lies between the heart and the spinal column.

The blood of a cardiac arrest patient is artificially circulated during CPR by cyclically compressing and releasing the chest. One theory that describes how artificial circulation is generated during CPR says that the patient's rigid sternum is pushed against the anterior of the heart during chest compression and the heart is squeezed between the sternum and the spinal column. The soft, flexible esophagus is not rigid enough to provide rear support for the heart. Therefore, the sternum must be pushed far enough to force the posterior of the heart against the rigid spinal column in order to produce blood circulation. For CPR to be effective, the blood flow produced must provide perfusion to the heart muscle, known as the myocardium, and the brain, known as the cerebrum, in order for these tissues to remain viable. For the most part, the method of CPR used today produces inadequate myocardial and cerebral perfusion.

In addition to artificial circulation, many patients also require a defibrillation countershock during CPR in order to restart their heart. Defibrillation countershock therapy involves placing two electrodes near the heart and inducing a flow of electrical current through the chest and heart and preferably through the left ventricle of the heart which is the largest part of the heart muscle that is fibrillating. The electrodes used are hand-held paddles or adhesive pads, either of which are placed at different positions on the external surface of the patient's chest, sides and/or back. A defibrillation countershock delivered with this electrode placement methodology is commonly called an external defibrillation countershock.

A sufficient electrical current density must be induced in the myocardium in order to defibrillate a fibrillating heart. Current density is defined as the amount of current per cross sectional area of tissue. In addition, the required minimum current density must depolarize at least a certain minimum critical mass of the left ventricle of the heart in order to achieve defibrillation. For any given total current induced in the chest during a defibrillation countershock, the current density in the myocardium is generally inversely proportional to the distance between the countershock electrodes. This distance will vary depending on the location of the electrodes and the size of the patient's chest. If the electrodes are widely separated, more of the total current will pass through non myocardial tissue. It is therefore advantageous to position the electrodes as close to the heart as possible in order to achieve defibrillation.

The machine used to deliver a defibrillation countershock as well as monitor and, when necessary, pace a patient's heart, is commonly called a defibrillator. All defibrillators used clinically today are described as energy defibrillators in that the person administering countershock therapy presets the amount of electrical energy to be delivered to the patient in the countershock. For any preset energy level, the total current and current density induced in the myocardium is generally inversely proportional to the electrical impedance of the tissues lying between the electrodes. Although the myocardium has a relatively low impedance to current flow, tissues such as bone have a high impedance. For instance, structures such as the sternum, ribs and spinal column have relatively high impedance to current flow. Some or all of these tissues interpose the electrodes during an external countershock. It is therefore advantageous to position the electrodes so that there is the least possible amount of non myocardial, high impedance tissue between them.

It is further advantageous to use the smallest amount of current necessary to defibrillate the heart of a patient in cardiac arrest. Excessive current and specifically excessive myocardial current density causes irreversible structural damage to the myocardial tissue.

Internal countershock therapy utilizes the most ideal electrode placement and offers the highest probability of achieving defibrillation. In this method, the pair of electrodes are placed on opposite sides of and touching the left ventricle of the exposed heart and the current is induced between the two electrodes. Under this circumstance, the distance between the electrodes is minimized and virtually no other tissues other than the myocardium interposes the electrodes. Virtually all of the current flows through the left ventricle of the heart. This electrode placement requires that the chest be opened in order to expose the heart. Therefore, it is typically only performed under sterile conditions in an operating room. This procedure is impractical in an emergency setting outside the operating room.

One newly proposed method of electrode placement meant to reduce the amount of high impedance tissue between the electrodes as well as reduce the distance between the electrodes involves placing one small electrode in the esophagus and a second electrode on the outer surface of the patient's chest. This is shown in U.S. Pat. No. 5,170,803. Similarly, U.S. Pat. No. 4,198,953 shows an esophageal electrode urged against the esophageal wall by a balloon. That patent refers to U.S. Pat. No. 4,090,518, described as suitable for use with the invention of that patent.

A second proposed orientation of electrodes consists of a pair of small electrodes at different spaced positions in the patient's esophagus. This is shown in U.S. Pat. No. 4,960,133. U.S. Pat. No. 4,706,688 also shows placement of multiple electrodes in the esophagus and uses a flaccid balloon to urge the electrodes toward the heart.

A third proposed orientation of electrodes consists of a small electrode placed in the stomach, forced upwardly against the top of the stomach wall until the stomach wall contacts the bottom of the heart. In this device, the second electrode needed for the countershock is placed on the patient's chest. This is shown in U.S. Pat. No. 5,197,491. None of these newly proposed electrode orientations utilize the stomach and the esophagus concurrently for countershock therapy. None of the devices which are placed in the esophagus function as rigid supports to enhance artificial circulation during CPR. Each of these proposed electrode orientations utilize an external electrode. Under this circumstance, the distance between the countershock electrodes may be reduced but is not minimized and high impedance tissues such as the sternum and ribs still interpose the electrodes.

A fourth proposed electrode orientation consists of six electrodes at different locations in the esophagus. Countershock current is passed from the proximal three electrodes to the distal three electrodes. Although the impedance is low with this electrode orientation, the heart does not interpose the electrodes but rather lies anterior to the electrodes and, therefore, a sizable portion of the current induced between the electrodes may pass through non myocardial tissue. This device also does not provide rigid support for the heart during CPR.

U.S. Pat. Nos. 5,056,532 and 5,179,952, while not directed to countershock, do show electrodes placed in the esophagus for pacing and monitoring. U.S. Pat. No. 5,056,532 also shows flaccid esophageal and stomach balloons for positioning the device but having no electrical function.

There are several inflatable devices described in the prior art that are placed in the esophagus during artificial ventilation and act as airway adjuncts by closing off the esophagus to allow air to flow primarily into the lungs. There are other devices which are placed in the esophagus to stop bleeding from the inner walls of the esophagus, and which are inflated to tamponade blood vessels along the esophageal wall. These devices are neither electrical adjuncts to defibrillation countershock, cardiac pacing or monitoring, nor mechanical adjuncts to CPR for treating cardiac arrest patients.

The need exists for an apparatus which enhances artificial circulation, and particularly enhances myocardial and cerebral perfusion, as well as simultaneously providing a more effective current pathway for defibrillation countershock without opening the chest by minimizing the distance between the electrodes and by positioning the electrodes so that there is virtually no tissues other than the myocardium interposed between the electrodes during the countershock.

BRIEF DISCLOSURE OF INVENTION

The invention is an improved apparatus for treating cardiac arrest patients, patients with arrhythmias, patients undergoing cardioversion, patients in shock, patients with a need for monitoring and patients in need of cardiac pacing. The apparatus has an expansible walled body for positioning in the patient's esophagus near the posterior of the patient's heart to provide a body which is sufficiently rigid to support the heart and aorta when they are compressed during CPR. It is very advantageous that the expansible walled body be a bladder constructed of essentially inelastic wall material so that when filled with a fluid, and preferably an essentially incompressible liquid, the bladder becomes essentially non-compliant and consequently will exhibit the necessary sufficient rigidity.

Another aspect of the invention comprises an improved heart compressing method for treating a cardiac arrest patient. The improved method comprises inserting an expansible walled body, sometimes referred to as a bladder, in the patient's esophagus posterior to the patient's heart. This esophageal bladder is filled with a gas or liquid and preferably an incompressible fluid for providing the sufficiently rigid platform near the posterior region of the heart. The heart is manually forced against the rigid platform to improve artificial circulation.

The improved apparatus further comprises an electrode attached to or part of the esophageal bladder for, in combination with a second and perhaps a third electrode and in conjunction with a defibrillator, inducing a flow of electrical current between certain combinations of the electrodes, through at least a portion of the heart.

The invention still further comprises an improved electrode placement method for defibrillating the heart of a cardiac arrest patient. The improved placement method comprises inserting a first electrode into the patient's esophagus posterior to the heart, inserting a second electrode into the patient's stomach near the heart and inducing a flow of electrical current between the electrodes. This improved electrode placement method also can further comprise attaching a third electrode to the outer surface of the patient near the heart and inducing a flow of current simultaneously from two of the electrodes to the remaining electrode. For example, electrical current can be induced to flow from the second and third electrodes to the first electrode in the esophagus. These electrode combinations also provide a means for cardiac pacing and cardiac monitoring.

Figure 1:
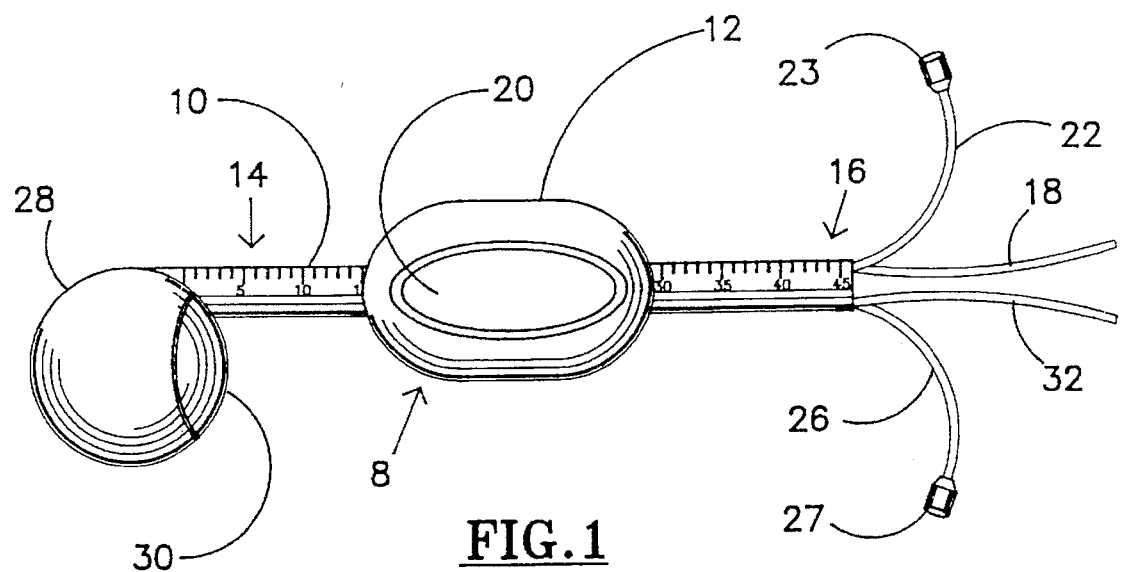
FIG. 1 is a top view illustrating the preferred embodiment of the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

Figure 2:
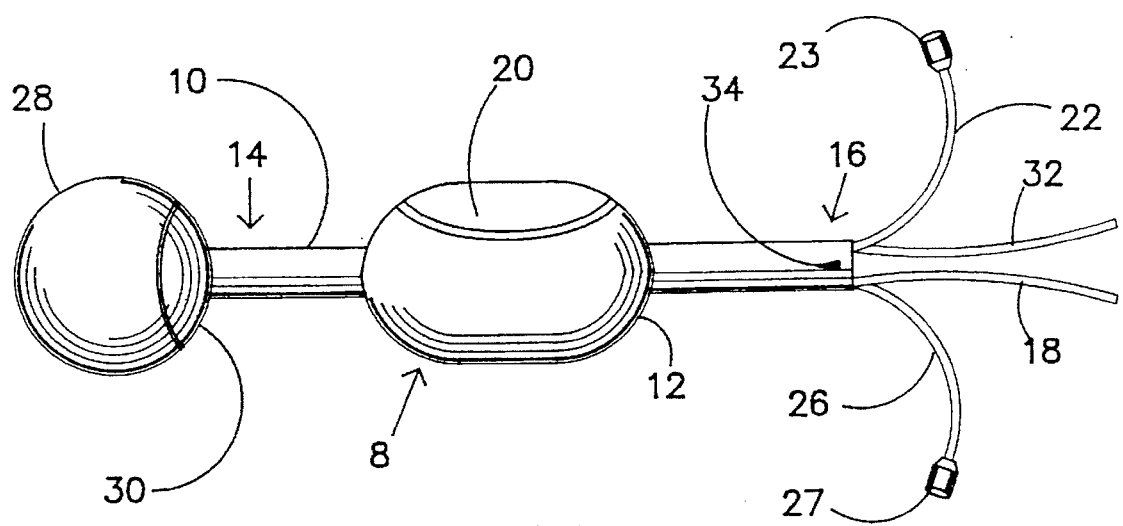
FIG. 2 is a side view illustrating the embodiment in FIG. 1.

The preferred embodiment illustrated in FIG. 1 and FIG. 2 is an apparatus 8, including a tube 10 which is flexible enough to be passed through the esophagus and into the upper region, or fundus, of the stomach, yet sufficiently rigid that rotation of one end of tube 10 will cause an equal rotation of the opposite end. The tube 10 is preferably approximately 45 centimeters long, has an internal, distal end region 14 which is extended into the internal organs of a patient, and an external, proximal end region 16 which remains outside of the patient when tube 10 is in its operable position.

An expansible walled body, preferably an elongated esophageal bladder 12 with flexible, substantially inelastic walls, is adhered to tube 10, at a location on tube 10 so that the esophageal bladder will be directly posterior to the heart when the device is in its operable position. The esophageal bladder 12 is approximately 10 centimeters in length and 4 centimeters in outer diameter in the preferred embodiment. The esophageal bladder 12 of FIGS. 1 and 2 extends circumferentially around the outer surface of tube 10, and the axis of the esophageal bladder 12 is aligned generally coaxially with the axis of tube 10.

A second walled body, preferably a spherical stomach bladder 28 approximately 10 cm in diameter, with flexible, preferably elastic, walls, is adhered to tube 10 at the internal end region 14 in a position at which the center of the stomach bladder 28 is radially offset from the axis of tube 10. A line extending from the axis of tube 10 completely through the stomach bladder 28 does not intersect the center of the stomach bladder 28 in the preferred embodiment, but passes eccentrically some distance from it.

An electrode wire 18 is embedded within the sidewall of tube 10, and extends from the external end region 16 through the sidewall to the esophageal bladder 12. An esophageal electrode 20 is attached to, such as by being integrally formed as a part of, the esophageal bladder 12. The wire 18 which is embedded in the sidewall of tube 10 is connected to the esophageal electrode 20.

A second electrode wire 32 is also embedded within the sidewall of tube 10 and extends from the external end region 16 through the sidewall of the tube 10 through the internal end region 14 and to the stomach bladder 28. A stomach electrode 30 is attached to and may also be integrally a part of, the stomach bladder 28. The wire 32 which is imbedded in the sidewall of tube 10 is connected to the stomach electrode 30.

A hollow fluid-conveying tube 22 is attached to the external end region 16 of the sidewall of tube 10. The lumen of the fluid-conveying tube 22 communicates with an internal passageway formed through the sidewall of tube 10. This passageway (not shown in FIGS. 1 and 2) extends through the sidewall of tube 10 from its connection with the fluid-conveying tube 22 into the interior of the esophageal bladder 12. Fluid forced through the fluid-conveying tube 22 passes through the lumen of tube 22, through the passageway formed through the sidewall of tube 10 and into the interior of the esophageal bladder 12. The fluid-conveying tube 22 has a leurlock type fitting 23 at its proximal end.

A second hollow fluid-conveying tube 26 is also attached to the external end region 16 of the sidewall of tube 10. The lumen of the fluid-conveying tube 26 communicates with a second internal passageway formed through the sidewall of tube 10. This passageway (not shown in FIGS. 1 and 2) extends through the sidewall of tube 10 from its connection with the fluid-conveying tube 26 into the interior of the stomach bladder 28. Liquid or gas forced through the fluid-conveying tube 26 passes through the lumen of the tube 26, through the passageway formed through the sidewall of tube 10 and into the interior of the stomach bladder 28. The fluid-conveying tube 26 has a leurlock type fitting 27 at its proximal end.

Figure 5:
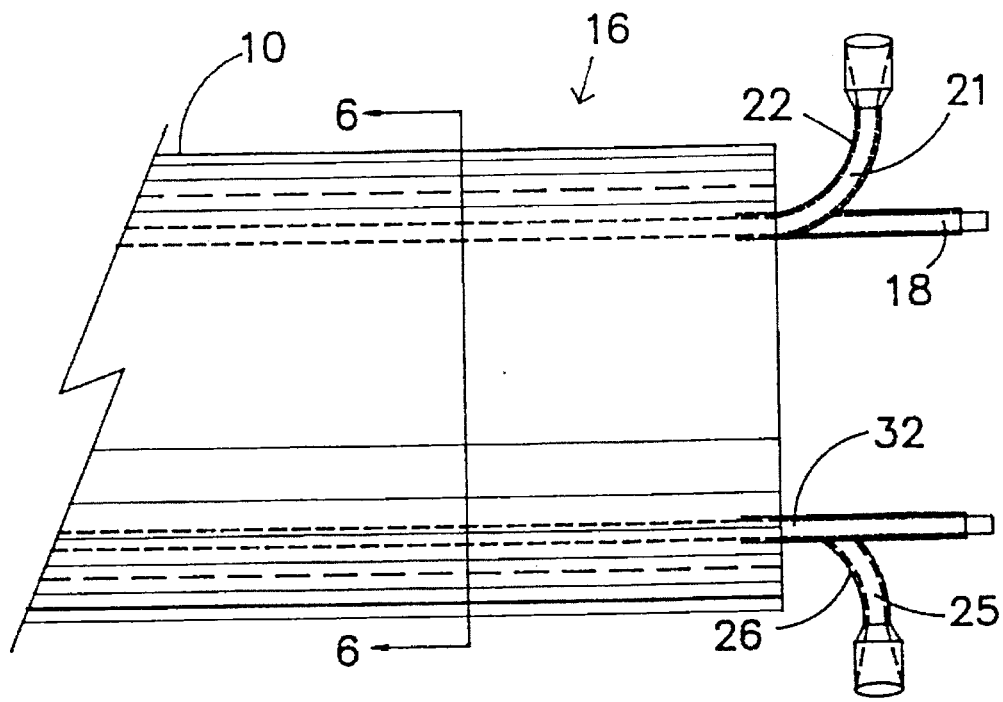
FIG. 5 is a detailed view of the end of the tube of the embodiment in FIG. 1 and 2.
Figure 6:
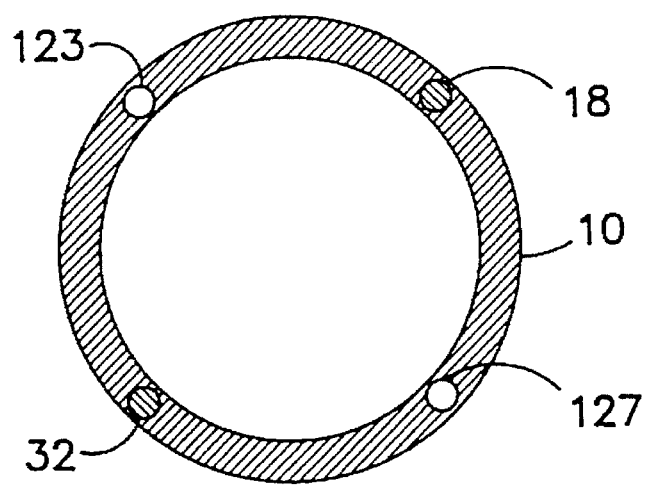
FIG. 6 is a view in section taken along the lines 6—6 of FIG. 5.

FIGS. 5 and 6 show the structural details at the external end 16 of the tube 10. The fluid-conveying tube 22, having a lumen 21 within it, is connected at the proximal or external end of tube 10 to passageway 123 formed in the wall of tube 10. Passageway 123 extends from the proximal end of tube 10 to an intermediate position of tube 10 at which it communicates with the interior of the esophageal bladder 12 (not shown in FIG. 5). Similarly, the fluid-conveying tube 26 is attached to the proximal end of tube 10, and its lumen 25 communicates with a passageway 127 formed through the wall of tube 10. Passageway 127 extends substantially the entire length of the tube 10, and communicates with the interior of the stomach bladder 28 (not shown in FIG. 5).

The wire 18 is connected to the proximal end of tube 10 and extends through the sidewall of tube 10 to an intermediate position at which it connects with the esophageal electrode 20 (not shown in FIG. 5). Similarly, a wire 32 attaches to the proximal end of tube 10 and extends through the sidewall of tube 10 substantially the entire length of tube 10 where it connects with the stomach electrode 30 (not shown in FIG. 5).

Figure 7:
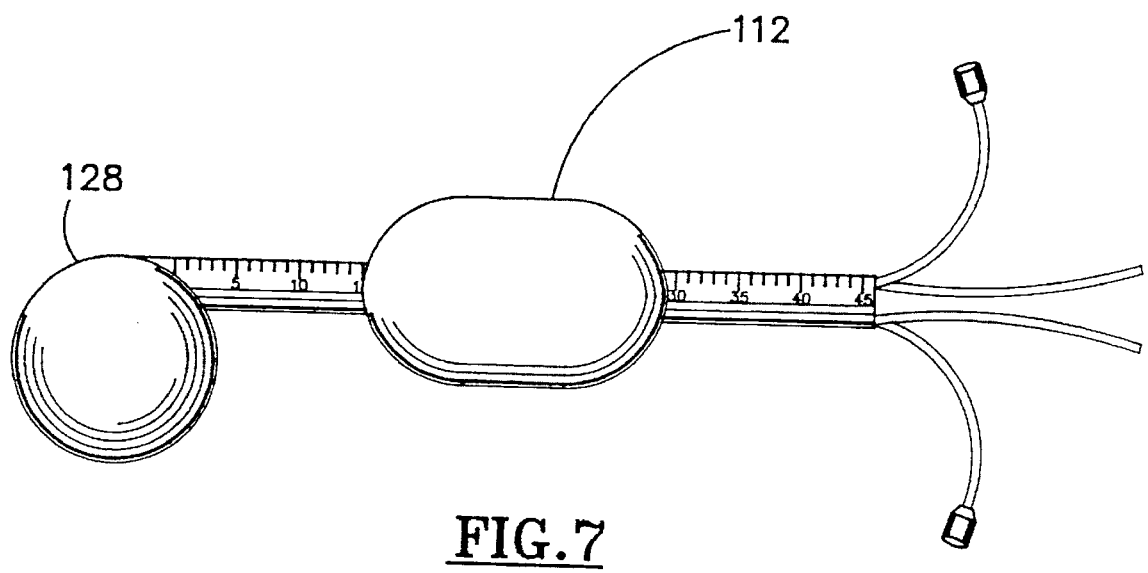
FIG. 7 is a top view illustrating esophageal and stomach bladders which have walls which are electrically conductive.

Electrodes 20 and 30 are attached to bladders 12 and 28. They can be attached to the outer surfaces of bladders 12 and 28 as thin, metallized films, or can be formed as an integral part of the bladder's sidewalls. Electrodes 20 and 30 can occupy either a portion of the outer surface area of bladders 12 and 28 as shown in FIGS. 1 and 2, or they can alternatively occupy the entire outer surface of the bladders 12 and 28, as shown in FIG. 7. For example, it is possible to form the bladder sidewalls from graphite- or silver-impregnated rubber or silicone which would make the entire wall of bladders 112 and 128 conductive and thereby function as electrodes.

As an alternative embodiment, it is possible to eliminate the stomach bladder and have an electrical contact made of a conductive metal which extends into the stomach. In addition to this, the stomach can be filled with a saline solution which is conductive, and the electrical current will pass from the electrode into the saline solution and through the heart to an electrode positioned on the opposite side of the heart.

A set of demarcations, preferably a set of highly visible lines, is formed on the outer surface of tube 10 and along its entire length. Adjacent demarcations are one centimeter apart. The demarcations are numbered consecutively starting with a demarcation at the internal end region 14 of tube 10. The demarcations and numbers form a scale with which to measure how far tube 10 is inserted into the esophagus and stomach. Another demarcation, preferably a highly visible arrow 34, is formed on the outer surface of tube 10 near the external end region 16 of tube 10. The arrow 34 marks the side of tube 10 indicating the direction in which the stomach bladder 28 is offset from the tube 10 axis for aiding in positioning the offset stomach bladder 28 when not visible, for example when within the patient's body.

Figure 3:
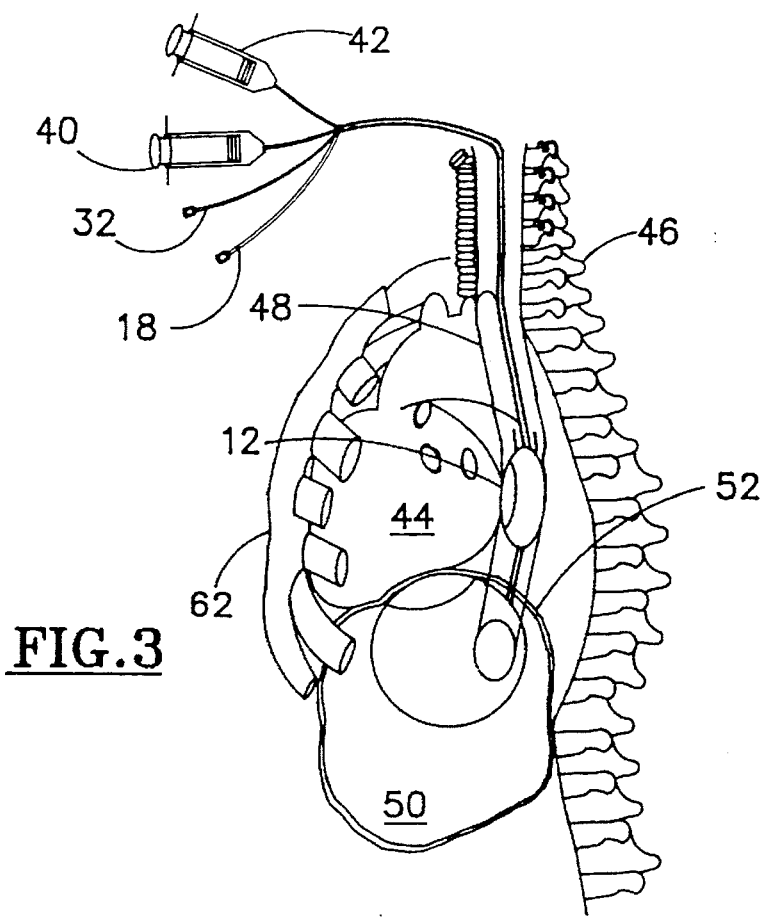
FIG. 3 is a side view in section illustrating a human chest cavity and showing the preferred embodiment of the present invention in its operable position.
Figure 4:
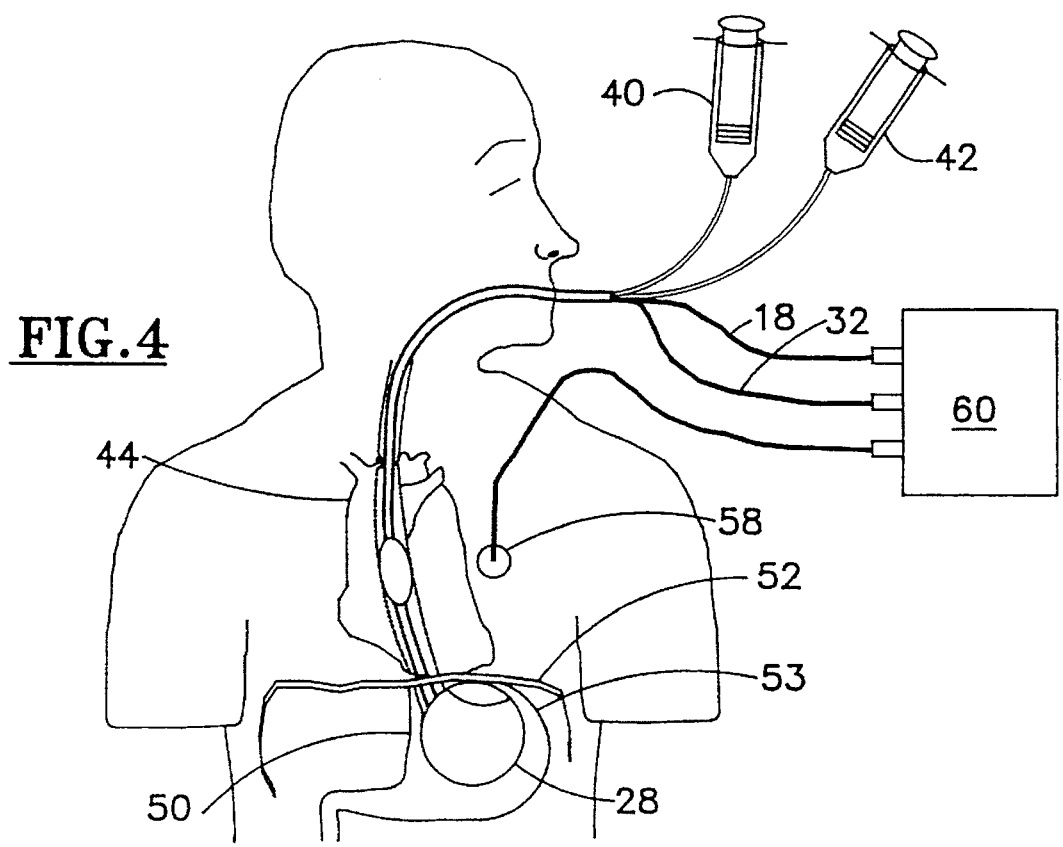
FIG. 4 is a frontal view in section illustrating the preferred position of the preferred embodiment of the present invention in its operable position.

In typical operation, the apparatus 8 illustrated in FIGS. 1 and 2 is placed in the preferred operable position as illustrated in FIG. 3 and 4 in the following manner. The sidewalls of bladders 12 and 28 are collapsed and folded around tube 10 so that they are as small and unobtrusive as possible. The internal, distal end region 14 of tube 10 is first inserted into the patient's mouth or nose and manually advanced through the esophagus 48 and into the fundus of the stomach 50. This action will position the esophageal bladder 12 approximately posterior to the heart 44. The external end region 16 of tube 10 will be left extending out of the mouth or nose of the patient.

Syringe 42 is attached to the fluid conveying tube 26 which communicates with the interior of the stomach bladder 28. Syringe 42 contains a liquid, preferably a conductive saline water solution, or a gas. The liquid or gas is injected into the stomach bladder 28 from the syringe 42, fully filling the stomach bladder 28. The filled stomach bladder 28 fills the fundus of stomach 50 just beneath the heart with preferably only the stomach wall 53 and the diaphragm 52 separating the bottom of the heart 44 from the top of the stomach bladder 28. The stomach electrode 30 is forced against the epithelial surface of the stomach 50, directly beneath the left ventricle of the heart 44 by applying a moderate degree of countertraction to tube 10. Only a small amount of tissue separates the stomach bladder 28 from the bottom of the heart 44 and the esophageal bladder 12 from the posterior of the heart 44.

A second syringe 40 is attached to the fluid-conveying tube 22 and a liquid, preferably a conductive saline water solution, is injected from the syringe 40 into the fluid-conveying tube 22 and into the esophageal bladder 12 while applying a moderate degree of countertraction to tube 10. As the esophageal bladder 12 is filled, the bladder sidewalls unfold, expanding the diameter of the esophagus 48 as bladder 12 reaches its fully filled size. A portion of the length of the esophagus 48 is then hardened and expanded due to the hardened and expanded esophageal bladder 12 within it. The electrode 20 on the fully filled esophageal bladder 12 contacts the epithelial surface of the esophagus 48 adjacent and posterior to the heart 44.

The esophagus 48 is naturally located between the heart 44 and the spinal column 46, as shown in FIG. 3. A portion of the upper region of the stomach 50 is naturally located directly beneath the bottom of the heart 44, separated by the diaphragm 52. Electrodes 20 and 30 occupy a significant portion of the sides of bladders 12 and 28 which are closest to the heart 44 so that current passing between electrodes 20 and 30 passes through the least amount of non myocardial tissue possible. This electrode orientation closely approximates that of an internal defibrillation countershock.

As illustrated in FIG. 4, the electrode wires 18 and 32 which are embedded in the sidewalls of tube 10, are connected to the electrodes 20 and 30 at their distal end and are connected to the defibrillator 60 at the proximal end. The defibrillator 60 is conventionally used for treating cardiac arrest patients by countershocking the heart. In addition, the defibrillator 60 is also designed for monitoring and pacing the heart. Defibrillator 60 is not considered to be part of the invention, but defibrillator 60 is used in combination with the invention. Defibrillator 60 functions in its conventional manner.

In the preferred embodiment, a flow of electrical current is induced between the stomach electrode 30 and the esophageal electrode 20, preferably passing through the left ventricle. The amount of energy and the other important variables of countershock are preset by the user in the conventional manner.

A third external, conventional electrode 58 can be attached to or positioned in contact with the patient's skin near the heart. A flow of electrical current may be induced between any pair of electrodes, in an attempt to defibrillate the heart of the cardiac arrest patient as well as pace and/or monitor the heart. Additionally, electrical current can flow between two electrodes to the third electrode to be certain that electrical current passes through the required minimum critical mass of myocardium. For example, it has been found to be advantageous to induce a flow of electrical current from both the stomach and an external electrode at the apex of the heart simultaneously to the esophageal electrode. There is also an advantage to inducing a flow of current from an electrode or a plurality of electrodes of a given surface area to one or more electrodes having a smaller surface area. The electrocardiogram (ECG) can be monitored from any electrode pair and the signal analyzed to determine the state of the heart during treatment. The heart can also be electrically paced through an electrode pair which may help to establish an organized depolarization/repolarization sequence for the heart muscle consistent with a normally functioning heart, as well as returning spontaneous circulation.

Because of the close proximity of the bladder electrodes to the heart tissue, a critical mass of myocardium will have a sufficient electrical current pass through it to defibrillate it. Because of the decrease in the amount of non myocardial high impedance tissue between the bladder electrodes and the heart, the impedance between these electrodes will be low and the impedance measured will mostly be characteristic of the impedance of the heart tissue. This means that a lower current may be necessary to create a sufficient current density to defibrillate the heart. This decreased current may decrease the amount of damage to the heart caused by a countershock. This electrode orientation closely approximates that of internal defibrillation countershock.

With the present invention, the current density through the left ventricle is maximized to maximize the probability of defibrillation. This maximization occurs due to the proximity of the electrodes to the left ventricle. An overly large heart will not require a different electrode orientation with respect to the heart using the present invention. An enlarged heart might actually increase the amount of current which flows through the left ventricle since a large heart will place the left ventricle in closer proximity to the electrodes.

The esophageal bladder, once filled, not only places an electrode close to the heart, but also serves as a platform against which the heart can be pressed to increase the artificial circulation of blood in the patient during CPR. Referring to FIG. 3, the esophagus 48 alone provides little support for the heart when the chest is compressed. The heart 44 is normally pushed back into the chest cavity in an attempt to compress it against the spinal column 46 by depressing sternum 62. With the esophageal bladder 12 in place and filled, the heart 44 is manually forced by the sternum 62 against the hardened and expanded esophagus 48 which is supported from the rear by the spinal column 46. The present invention decreases the distance the sternum 62 must be depressed to squeeze the heart 44 and, therefore, aids in more effectively compressing the heart 44. Since the aorta is near the esophagus 48, the aorta may also be compressed somewhat, increasing aortic pressures which will improve myocardial and cerebral perfusion. Defibrillation is positively correlated with coronary perfusion pressure. Improving myocardial perfusion during the use of the present invention, therefore, increases the probability of defibrillation.

When the stomach bladder is filled and countertraction is applied, inferior diaphragmatic excursion is reduced during chest compression. This increases intrathoracic pressure during chest compressions and ventilations, which increases CPR-produced perfusion.

When the esophageal bladder 12 is in position behind the posterior of the heart 44, at least two advantages are realized.

First, the esophageal electrode 20 is placed in close proximity to the heart 44 to allow for countershock which has a high likelihood of defibrillating the heart. Additionally, the esophageal bladder 12 hardens and expands the esophagus 48 to provide a platform posterior of the heart 44 against which the heart 44 and aorta is compressed to provide improved artificial air circulation during CPR. The same device provides an electrode near the heart, while simultaneously providing a platform behind the heart which improves the circulatory effects of CPR.

Finally, because tube 10 is hollow, it can also function as a passageway for the purpose of gastric pumping.

It is preferred that the esophageal bladder be inelastic so that it may be filled with a liquid or with a gas and maintained at a sufficient pressure so that it will provide a sufficiently firm and less deformable surface which will support the heart and aorta when they are pressed against the bladder and yet the esophageal bladder will not overexpand and cause tissue trauma. The use of an incompressible fluid with an expansible-walled body having inelastic walls provides an essentially rigid platform for supporting the compressed heart and aorta during cardiopulmonary resuscitation.

It is preferred that the esophageal bladder be essentially inelastic and that it be filled with an essentially incompressible fluid, once properly positioned in the esophagus. In this preferred embodiment, the filled esophageal bladder will provide a sufficiently firm and nondeformable surface that will support the heart and aorta when they are pressed against the bladder during CPR. It is preferred that during a properly administered CPR chest compression, which is defined by the American Heart Association as a 1½ to 2 inch chest excursion, the anteroposterior dimension of the filled esophageal bladder will not decrease by more than 5 percent. Therefore, a fluid and a bladder wall material are preferably selected having the parameters of fluid compressibility and bladder wall elasticity which are sufficiently incompressible and inelastic to give no more than the 5 percent decrease. This preferred embodiment has the additional advantage of not overexpanding when it is filled and, therefore, not causing tissue damage.

The expansible walled bodies are not necessarily limited to fluid filled bodies, although they are preferred. For example, bodies can be expanded by mechanical mechanisms known in the art. Such mechanically expansible devices would include mechanisms similar to those found in umbrellas or multi-wire remote grippers.

While certain preferred embodiments of the present invention have been disclosed in detail, it is to be understood that various modifications may be adopted without departing from the spirit of the invention or scope of the following claims.

We claim:

1. In an apparatus for treating cardiac patients, having at least two electrodes connected to a defibrillator, an improved apparatus comprising:
   (a) an expansible walled body forming a bladder for positioning in a patient's esophagus near the posterior of the patient's heart said body having walls which are sufficiently inelastic to provide a rigid support against which the heart and aorta can be forced and compressed, wherein the anteroposterior dimension of the bladder is decreased by not more than about five percent during a properly administered CPR chest compression; and
   (b) a first electrode of said two electrodes attached to the expansible walled body for, in combination with a second electrode of said two electrodes and a defibrillator, inducing a flow of electrical current between the electrodes, through at least a portion of the heart.

2. An apparatus in accordance with claim 1 wherein the expansible walled body comprises a fluid fillable bladder.

3. An apparatus in accordance with claim 2 wherein the bladder has flexible, substantially inelastic walls.

4. An apparatus in accordance with claim 3 and further comprising the second electrode sufficiently spaced from the first electrode, by a spacing means connected to the electrodes, for positioning the second electrode in the patient's stomach near the heart for inducing a flow of electrical current between the second electrode in the stomach and the first electrode in the esophagus, through at least a portion of the heart.

5. An apparatus in accordance with claim 4 wherein the second electrode is attached to a second fluid fillable expansible bladder having flexible, walls.

6. An apparatus in accordance with claim 5 wherein the second bladder has elastic walls.

7. An apparatus in accordance with claim 5 wherein the apparatus further comprises a third electrode attached to an outer surface of the patient near the heart.

8. An apparatus in accordance with claim 5 wherein each bladder is attached to a substantially rigid insertion tube for manually inserting the bladders into the patient's body and manipulating the position of the bladders within the body as well as applying countertraction to the stomach.

9. An apparatus in accordance with claim 8 wherein the insertion tube has two electrode wires and two fluid-conveying tubes, each wire extending from a different one of the electrodes to the proximal end of the insertion tube, and each fluid conveying tube extending from the interior of a different bladder to the proximal end of the insertion tube, for conveying electrical energy to each bladder electrode and for conveying fluid to each bladder.

10. An apparatus in accordance with claim 9 wherein the electrode wires and the fluid conveying tubes are embedded in the sidewalls of the insertion tube.

11. An apparatus in accordance with claim 9 wherein the second bladder is eccentrically offset from the axis of the insertion tube.

12. An apparatus in accordance with claim 11 wherein the insertion tube has visible demarcations on its exterior surface for indicating the orientation of the stomach bladder and the depth to which the insertion tube has been inserted into the esophagus and stomach.

13. An apparatus in accordance with claim 8 wherein at least a portion of an outer wall surface of the first and second bladders are electrically conductive.

14. An apparatus in accordance with claim 13 wherein the entire outer wall surface of the first and second bladders are electrically conductive.

15. An apparatus in accordance with claim 13 wherein the bladder positioned in the esophagus is elongated and the bladder positioned in the stomach is spheroidal.

16. An improved heart compressing method for treating a cardiac arrest patient comprising:
   (a) inserting an expansible walled bladder having flexible inelastic walls into an esophagus of the patient near the heart;
   (b) filling and expanding the expansible walled bladder with a fluid to a pressure which is effective for providing a platform near a posterior region of the heart which is sufficiently rigid to support the heart and aorta during compression, wherein the anteroposterior dimension of the bladder is decreased by not more than about five percent during a properly administered CPR chest compression; and (c) forcing and compressing the heart and aorta against the platform provided by the expansible walled bladder.

17. A method in accordance with claim 16 wherein the method further comprises inserting a second expansible bladder having flexible, elastic walls into the stomach of the patient near the heart and expanding the bladder.

18. An improved electrode placement method for heart defibrillation of a cardiac arrest patient comprising:

(a) inserting a first electrode into a patient's esophagus near a posterior region of a heart;

(b) inserting a second electrode into the patient's stomach near the heart; and (c) inducing a flow of electrical current between the electrodes.

19. A method in accordance with claim 18 wherein the first and second electrodes are attached to first and second fillable bladders having flexible, fillable walls, and the method further comprises filling the bladders by injecting fluid into them.

20. A method in accordance with claim 19 wherein the method further comprises attaching a third electrode to an outer surface of the patient's body.

21. A method in accordance with claim 20 wherein the method further comprises inducing a flow of electrical current from both the second and third electrodes to the first electrode in the esophagus.

22. A method in accordance with claim 19 wherein the method further comprises pacing and monitoring the heart using said electrodes.

* * * * *